United States Patent [19]
Hemmeter

[11] Patent Number: 4,589,405
[45] Date of Patent: May 20, 1986

[54] THERMAL ACTIVATED PENILE PROSTHESIS

[76] Inventor: George T. Hemmeter, 4125 Black Point Rd., Honolulu, Hi. 96816

[21] Appl. No.: 660,216

[22] Filed: Oct. 12, 1984

[51] Int. Cl.$^4$ ............................................. A61F 5/00
[52] U.S. Cl. ...................................... 128/79; 623/11; 623/26
[58] Field of Search ....................... 128/79; 623/11, 12

[56] References Cited

U.S. PATENT DOCUMENTS 4,449,520  5/1984  Palamar et al. ........................ 3/1 X
4,498,466  2/1985  Pomeranz ........................ 604/349 X

FOREIGN PATENT DOCUMENTS 0072167  2/1983  European Pat. Off. ............... 79 A/

Primary Examiner—Stephen C. Pellegrino

[57] ABSTRACT

A pair of inflatable tubes for implanting in the corporal cavernosa of a man's penis to restore potency. These prosthesis tubes contain a small charge of a hydrocarbon fluid which when heated to a temperature above 98.3° F. boils, building up a gas pressure and causing a stiffening of the prosthesis tubes. When the prosthesis is cooled below 98.3° F. the gas condenses and allows the prosthesis to go limp again. The use of a heat sensitive hydrocarbon in the prosthesis eliminates the need for a pump as a prime mover to cause an erection.

1 Claim, 6 Drawing Figures

THERMAL ACTIVATED PENILE PROSTHESIS

BACKGROUND OF THE INVENTION

1. Field of the Invention.

This invention is a penile prosthesis used to:

a. Restore potency to older men who have lost their potency with aging.

b. Restore potency to men who have lost their potency due to a prostatectomy operation.

c. To enable young men who by nature are impotent, to gain potency.

2. Description of the Prior Art.

There are three types of penile prosthesis in use today: The rigid type; the semi-rigid type; and the inflatable type. Each of these prosthesis has limitations and disadvantages.

The rigid type penile prosthesis causes a continuous erection of the penis which may be a discomfort and an embarrassment to the recipient.

The semi-rigid type penile prosthesis is an improvement over the rigid type in that the recipient can fold the penis at its mid-section which is more comfortable to the user.

The inflatable type penile prosthesis consists of two inflatable tubes for implanting in the corporal cavernosis of the penis. When deflated the penis is limp and normal. To cause an erection, a valve implanted in the scrotum is closed, and then a pump, also located in the scrotum, is operated by squeezing it through the walls of the scrotum operated to build up pressure in the prosthesis tubes. Liquid used in this prosthesis is contained in a reservoir implanted in the lower belly of the body. This prosthesis and its connecting tubeing is cumbersome. Implantation is demanding upon the talents of the surgical team. The recipient must learn to operate the apparatus skilfully and without over pressurizing the system.

SUMMARY OF THE INVENTION

When a man reaches sixty years of age or has a prostatectomy operation, he will probably become impotent. To gain potency perhaps the simplest way is but to have a penile prosthesis implant.

I have invented a new type penile prosthesis that is "thermally activated" thus eliminating the need for a pump as a prime mover. It consists, essentially, of one or more, thin, supple, collapsed, plastic or rubber-like tubes, void of air and partially filled with a limited amount of Normal-tentain Hydrocarbon. N-tentain ($C_5H_{12}$) is a liquid having a boiling point of 97.2 Deg.F. Other liquids having similar thermal characterists to N-tentain could be used. For example; if it is desired to retard the action in the prosthesis, Pentene-2 ($C_5H_{10}$) or Beta-Amylene ($C_5H_{10}$) each having a boiling point of 98.2 Deg.F., could be substituted. There are possibly other substitutes.

After the prosthesis is implanted in the penis and its temperature exceeds the boiling point of the activator liquid, it gassifies and the penis is erected. Heating of the prosthesis may be accomplished either by sexual excitement or by taking a warm shower, or by using a heating pad, etc.

After copulation and the penis cools to normal temperatures, (i.e. below boiling point of the activator), the hydrocarbon gas in the prosthesis condenses, forming a liquid of minimal volume in the prosthesis, and the penis will grow limp again.

I do not know of a penile prosthesis that uses a chemical that is thermally activated as a prime mover to cause a penile erection like my invention. All the recipient need do to have an erection is to become sexually excited or to apply heat to his private area. Erection will occur. After copulation the penis cools to normal temperature and becomes naturally limp. Mechanical manipulations by the recipient is minimal and embarrassment to the man is eliminated.

Thermal activation of the penile prosthesis to cause erection is quite natural and should be readily acceptable to most impotent men. Potency can now be restored and activated with dignity.

OBJECT OF THE INVENTION

An object of this invention is to provide a means by which a penile prosthesis implanted in the penis of an impotent man permits him to have a penile erection.

Another object of this invention is to provide a penile prosthesis that is thermally activated to cause an erection of the penis.

Another object of this invention is to provide a prosthesis that is thermally activated to restore the penis to limpness.

Another object of this invention is to provide a simple, one-element, penile prosthesis that goes through the complete cycle from penile limpness to erection and return to limpness without operating mechanical devices.

Another object of this invention is to provide a prosthesis that is simple to implant.

Other objectives of this invention will be readily apparent from reviewing the following detailed description, together with the accompanying drawings.

DESCRIPTION OF PREFERRED EMBODIMENT

Figure 1:
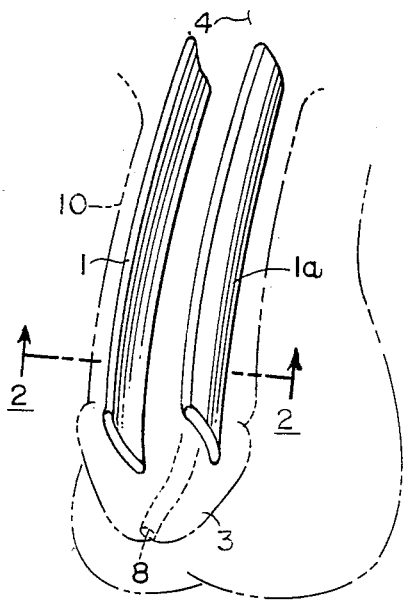
FIG. 1 is a view of a man's limp penis showing two prosthesis tubes implanted in the penis.

Before explaining the present invention in detail, it is to be understood that this invention is not limited in its application to the details of construction and arrangements of parts illustrated in the accompanying drawings and the specification of materials in use, since the invention is capable of other embodiments, and of being practiced or carried out in various ways.

Also, it is to be understood that the phraseology or terminology employed herein is for the purpose of description and not of limitation.

I have invented a new type penile prosthesis that is thermally activated as a prime mover.

It consists, essentially, of one, or more, thin, supple, collapsed, plastic or rubber-like tubes, void of air and partially filled with a limited amount of a liquid heat sensitive hydrocarbon.

N-tentain ($C_5H_{12}$) a liquid having a boiling point of 97.2 Deg.F. Other liquids having similar thermal characteristics could be used. Example; if it is desired to retard the operation of the prosthesis, Liquid Pentene-2 ($C_5H_{10}$) or Beta Amylene ($C_5H_{10}$) of the Olefin series, each of which boils at 98.2 Deg.F., could be substituted.

After the thermally actuated penile prosthesis is implanted in the penis, and its temperatures exceed the boiling point of the liquid activated in the prosthesis, the liquid boils, building up a gas pressure in the prosthesis tube, extending it and, as a result, the penis is erected.

Heating the penis and the prosthesis may be caused either by sexual excitement or by taking a warm shower or by using a heating pad., etc.

Referring now to the drawings wherein like reference numerals refer to like and corresponding parts through the several views.

The preferred embodiments of this invention are disclosed in FIGS. 1–4 inclusive.

This invention is a thermally activated penile prosthesis. It consists of one, or more, thin, supple, collapsed, plastic tubes of suitable length to fit the various sizes of the recipients corporal cavernosas.

The prosthesis tube length extends from the head of the penis into the recipient's body when implanted.

FIG. 1 shows two collapsed tubes, 1 and 1a implanted in the corporal cavernosas of the penis. They are essential parts of the prosthesis. They are constructed of thin plastic or rubber-like material and reach from the glan 3 to the pelvic area of a man's body. During manufacture the tubes 1 and 1a are evacuated of all air, then sparely charged with a limited amount of a temperature sensitive hydrocarbon fluid 7 and 7a such as Pentain which has a boiling point slightly under normal body temperature i.e. 98.3° F.

When heat is applied to the penis it heats the emplanted prosthesis tubes and their contents causing the chemical to boil and gassify thereby building up a pressure in the prosthesis tubes.

Figure 2:
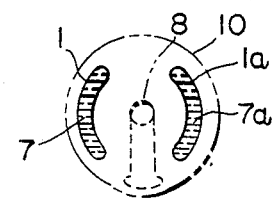
FIG. 2 is a simulated cross-section of a limp penis with a pair of deflated, liquid-filled prosthesis tubes in place, at liquid temperatures below the boiling point of said liquid.

FIG. 2 is a section 2—2 of the penis before applying heat above the body temperature. Note that the tubes 1 and 1a are collapsed and that they contain liquid 7 and 7a and no gas. The tubes do not obstruct the urinary canal.

Figure 3:
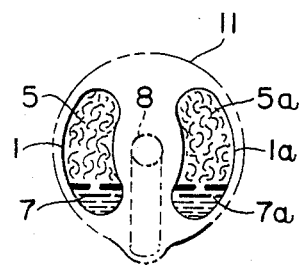
FIG. 3 is a simulated cross-section of an erected penis with a pair of expanded prosthesis tubes filled with hydrocarbon gas and liquid, at temperatures above the boiling point of said liquid.

When heat is applied to the penis as noted above, the boiling chemical gassifies as shown in 5 and 5a of FIG. 3. Boiling stops when the pressure in the tubes raises the boiling temperature of the liquid (Boyles law) leaving a portion of the liquid 7 and 7a intact.

Figure 4:
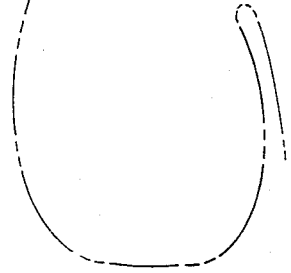
FIG. 4 is a side view of an erected penis showing the expanded prosthesis tube filled with gas and liquid that has caused the erection.

The gas pressure in the prosthesis tube acts as the prime mover, stiffening the expanded tubes and causing an erection of the penis as shown in FIG. 4.

When the penis is cooled after copulation the activator gas condenses to a liquid again. Without a gas pressure the prosthesis collapses and the penis grows limp again.

FIG. 3 shows a simulated section 3—3 of FIG. 4 through an erected penis 11 in which the prosthesis tubes 1 and 1a have been expanded by gas 5–5a from the boiling liquid 7 and 7a. The urinary canal is 8.

FIG. 4 is a side view of an erected penis 11, said erection is caused by gas 5a and 5 of FIG. 3 from the boiling liquid 7a and 7 of FIG. 3 expanding the prosthesis tubes 1 and 1a thus causing said erection.

Figure 5:
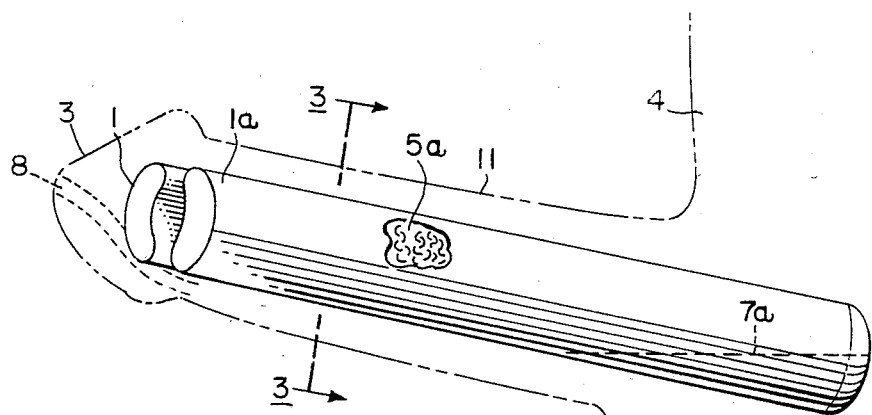
FIG. 5 is a simulated cross-section of a limp penis with a deflated liquid-filled prosthesis tube in place and at temperatures below the boiling point of said liquid.
Figure 5:
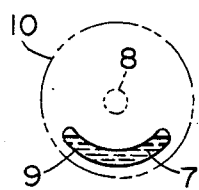

FIG. 5 shows a simulated cross-section of a limp penis 10 in which the prosthesis consists of a single tube 9 said tube is sparingly filled with a thermal-sensitive liquid 7 such as N-tentain. The temperature of the prosthesis tube 9 is below the boiling point of said liquid. Here, also, the prosthesis tube 9 is constructed of a thin, flexible, plastic material.

Figure 6:
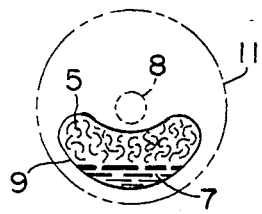
FIG. 6 is a simulated cross-section of an erected penis with an expanded prosthesis tube filled with hydrocarbon gas and liquid at temperatures above the boiling point of said liquid.

FIG. 6 shows a simulated cross-section of an erected penis 11 with the prosthesis tube 9 expanded by gas 5 from the boiling liquid 7, thus causing an erection of the penis 11.

My invention fills the need to restore potency to both young men and elderly men who are impotent.

Men who have undergone a prostatectomy operation resulting in impotency may find that their love life has suffered. This prosthesis may alter that situation.

The 'thermally activated' penile prosthesis will appeal to most men in their selection of a penile prosthesis for implantation into their body because it is simple to operate without embarrassment to either the recipient or to his partner. After implantation the thermally activated prosthesis is unnoticable on the man's body.

Of the three other penile prosthesis available, the 'thermally activated' prosthesis is less apt to be damaged by rough athletic treatment or from accidents.

I claim as my invention

1. A penile prosthesis device comprising a pair of sealed tubes, sized and shaped for implantation in the corpora cavernosa of the penis, said tubes made of a thin, supple, hydrocarbon compatible plastic material, with each tube partially filled with either Pentene −2 ($C_5H10$) or Beta-Amylene ($C_5H10$), said tubes in the normal state being collapsed and void of air, said tubes being inflated by increasing the temperature of the hydrocarbon above the boiling point to create a gas pressure within the tube.

* * * * *